(12) United States Patent
Anderson et al.

(10) Patent No.: US 8,632,772 B2
(45) Date of Patent: Jan. 21, 2014

(54) METHODS OF TREATING MULTIPLE MYELOMA USING COMBINATION THERAPIES BASED ON ANTI-CS1 ANTIBODIES

(75) Inventors: Kenneth C. Anderson, Wellesley, MA (US); Yu-Tzu Tai, Newton, MA (US)

(73) Assignee: Dana-Farber Cancer Institute, Boston, MA (US)

( * ) Notice: Subject to any disclaimer, the term of this patent is extended or adjusted under 35 U.S.C. 154(b) by 628 days.

(21) Appl. No.: 11/835,257

(22) Filed: Aug. 7, 2007

(65) Prior Publication Data

US 2008/0152646 A1 Jun. 26, 2008

Related U.S. Application Data

(60) Provisional application No. 60/836,185, filed on Aug. 7, 2006, provisional application No. 60/944,262, filed on Jun. 15, 2007.

(51) Int. Cl.
*A61K 39/395* (2006.01)
(52) U.S. Cl.
USPC ........................ 424/130.1; 514/1.1; 424/277.1
(58) Field of Classification Search
None
See application file for complete search history.

(56) References Cited

U.S. PATENT DOCUMENTS

| | | | |
|---|---|---|---|
| 2004/0029832 A1* | 2/2004 | Zeldis | 514/58 |
| 2005/0025763 A1* | 2/2005 | Williams et al. | 424/144.1 |
| 2006/0024296 A1* | 2/2006 | Williams et al. | 424/133.1 |

FOREIGN PATENT DOCUMENTS

| | | | |
|---|---|---|---|
| WO | 2005/102387 A2 | 11/2005 | |
| WO | 2008/019376 A2 | 2/2008 | |
| WO | 2008/019378 A1 | 2/2008 | |
| WO | 2008/019379 A2 | 2/2008 | |

OTHER PUBLICATIONS

Mesh word search result from NCBI, Apr. 23, 2009.*
Richardson et al., "A Phase 2 study of Bortezomib in relapsed,refractory myelmoa," N Engl J Med, 348:2609-2617 (Jun. 2003).
Kumar and Rajkumar, "Thalidomide and lenalidomide in the treatment of multiple myeloma," European J Cancer, 42(2006):1612-1622, (Jul. 2006).
Tai et al., "Killing of drug-sensitive and resistant myeloma cells and disruption of their bone marrow stromal intersection by HuLuc63, a novel humanized anti-CS1 monoclonal antibody," Blood (ASH Annual Meeting Abstracts) 2006:108: Abstract 3470 (2003).
Richardson et al., "Immunomodulatory drug CC-5013 overcomes drug resistance and is well-tolerated in patients with relapsed multiple myeloma," Blood, 100(9):3063-3067 (Nov. 2002).
International Search Report and Written Opinion for PCT Application No. PCT/US2007/075404, dated Feb. 2, 2008.
International Search Report and Written Opinion for PCT Application No. PCT/US2007/075403, dated Jan. 16, 2008.
Tai et al., "Anti-CS1 humanized monoclonal antibody HuLuc63 inhibits myeloma cell adhesion and induces antibody-dependent cellular cytotoxicity in the bone marrow milieu." Blood. Oct. 9, 2007; [Epub ahead of print].
Afar et al., "Anti-myeloma activity of HuLuc63 alone and in combination with bortezomib." Haematologica 92 (6) s2: 146, 2007. (Abstract PO-530).
Rice et al., "HuLuc63 in Combination Regimens with Conventional and Targeted Therapies Has Additive and Synergistic Anti-Tumor Activity in Pre-Clinical Models of Myeloma." Blood (ASH Annual Meeting Abstracts), Nov. 2007; 110:2517.
Sonneveld et al., "Changing concepts in multiple myeloma: from conventional chemotherapy to high-dose treatment" Eur J Cancer. Jan. 2003:39(1):9-18.
Jagannath S., "Treatment of myeloma in patients not eligible for transplantation." Curr Treat Options Oncol. May 2005;6(3):241-53.
Bruno et al., "New drugs for treatment of multiple myeloma." Lancet Oncol. Jul. 2004;5(7):430-42.
Lee et al., "DTPACE: an effective, novel combination chemotherapy with thalidomide for previously treated patients with myeloma." J Clin Oncol. Jul. 15, 2003;21(14):2732-9.
Boles et al., "Molecular cloning of CS1, a novel human natural killer cell receptor belonging to the CD2 subset of the immunoglobulin superfamily." Immunogenetics. 2001;52(3-4):302-7.
International Search Report and Written Opinion for PCT Application No. PCT/US2007/075401, dated May 15, 2008.
Bouchon et al., "Cutting Edge: Activation of NK Cell-Mediated Cytotoxicity by a SAP-Independent Receptor of the CD2 Family," *The Journal of Immunology*, vol. 167, pp. 5517-5521 (2001).
Dimopoulos et al., "Lenalidomide plus Dexamethasone for Relapsed or Refractory Multiple Myeloma," *New England Journal of Medicine*, vol. 357, pp. 2123-2132 (2007); including a Correction (N. Engl J. Med 2009; 361:544-a, 1 page).
Durie et al., "International Uniform Response Criteria for Multiple Myeloma," Leukemia, vol. 20, pp. 1467-1473 (2006).
Rajukumar et al., "Lenalidomide Plus High-Dose Dexamethasone Versus Lenalidomide Plus Low-Dose Dexamethasone As Initial Therapy for Newly Diagnosed Multiple Myeloma: An Open-Label Randomised Controlled Trial," *The Lancet Oncology*, Early Online Publication doi:10.1016/S1470-2045(09)70284-0, 9 pp., 2009.
Weber et al., "Lenalidomide plus Dexamethasone for Relapsed Multiple Myeloma in North America," *New England Journal of Medicine*, vol. 357, pp. 2133-2142 (2007).
Zonder et al., "Phase I Study of Elotuzumab (HuLuc63) in Phase I Study of Elotuzumab (HuLuc63) in Relapsed/Refractory Multiple Myeloma," Blood [50th Annu. Meet. Am. Soc. Hematol. (Dec. 6-9, San Francisco) 2008], vol. 112, No. 11: Abst 2773 (2008).
Guidance for Industry, Investigators, and Reviewers: Exploratory IND Studies, FDA Center for Drug Evaluation and Research (2006).
Printout from Cancer Research UK dated Jul. 21, 2010.
FDA Guidance on General Considerations for Clinical Trials, Federal Register / vol. 62, No. 242, pp. 66113-66119 (1997).
Campell and Berenson, Current Protocols in Pharmacology 14.9.1-14.9-22 (2008).
Hwang et al., The Scientific World Journal 6:1475-1503 (2006).

\* cited by examiner

*Primary Examiner* — Lei Yao
(74) *Attorney, Agent, or Firm* — Dechert LLP

(57) ABSTRACT

Compositions and methods for treating MM are provided herein.

4 Claims, 5 Drawing Sheets

2. BACKGROUND

SEQUENCE LISTING

```
<160> NUMBER OF SEQ ID NOS: 6

<210> SEQ ID NO 1
<211> LENGTH: 335
<212> TYPE: PRT
<213> ORGANISM: Homo sapiens

<400> SEQUENCE: 1

Met Ala Gly Ser Pro Thr Cys Leu Thr Leu Ile Tyr Ile Leu Trp Gln
1               5                   10                  15

Leu Thr Gly Ser Ala Ala Ser Gly Pro Val Lys Glu Leu Val Gly Ser
            20                  25                  30

Val Gly Gly Ala Val Thr Phe Pro Leu Lys Ser Lys Val Lys Gln Val
        35                  40                  45

Asp Ser Ile Val Trp Thr Phe Asn Thr Thr Pro Leu Val Thr Ile Gln
    50                  55                  60

Pro Glu Gly Gly Thr Ile Ile Val Thr Gln Asn Arg Asn Arg Glu Arg
65                  70                  75                  80

Val Asp Phe Pro Asp Gly Gly Tyr Ser Leu Lys Leu Ser Lys Leu Lys
                85                  90                  95

Lys Asn Asp Ser Gly Ile Tyr Tyr Val Gly Ile Tyr Ser Ser Ser Leu
            100                 105                 110

Gln Gln Pro Ser Thr Gln Glu Tyr Val Leu His Val Tyr Glu His Leu
        115                 120                 125

Ser Lys Pro Lys Val Thr Met Gly Leu Gln Ser Asn Lys Asn Gly Thr
    130                 135                 140

Cys Val Thr Asn Leu Thr Cys Cys Met Glu His Gly Glu Glu Asp Val
145                 150                 155                 160

Ile Tyr Thr Trp Lys Ala Leu Gly Gln Ala Ala Asn Glu Ser His Asn
                165                 170                 175

Gly Ser Ile Leu Pro Ile Ser Trp Arg Trp Gly Glu Ser Asp Met Thr
            180                 185                 190

Phe Ile Cys Val Ala Arg Asn Pro Val Ser Arg Asn Phe Ser Ser Pro
        195                 200                 205

Ile Leu Ala Arg Lys Leu Cys Glu Gly Ala Ala Asp Asp Pro Asp Ser
    210                 215                 220

Ser Met Val Leu Leu Cys Leu Leu Leu Val Pro Leu Leu Leu Ser Leu
225                 230                 235                 240
```

```
Phe Val Leu Gly Leu Phe Leu Trp Phe Leu Lys Arg Glu Arg Gln Glu
                245                 250                 255

Glu Tyr Ile Glu Glu Lys Lys Arg Val Asp Ile Cys Arg Glu Thr Pro
            260                 265                 270

Asn Ile Cys Pro His Ser Gly Glu Asn Thr Glu Tyr Asp Thr Ile Pro
        275                 280                 285

His Thr Asn Arg Thr Ile Leu Lys Glu Asp Pro Ala Asn Thr Val Tyr
    290                 295                 300

Ser Thr Val Glu Ile Pro Lys Lys Met Glu Asn Pro His Ser Leu Leu
305                 310                 315                 320

Thr Met Pro Asp Thr Pro Arg Leu Phe Ala Tyr Glu Asn Val Ile
                325                 330                 335

<210> SEQ ID NO 2
<211> LENGTH: 227
<212> TYPE: PRT
<213> ORGANISM: Artificial
<220> FEATURE:
<223> OTHER INFORMATION: hu50/mu50: amino acids 1-151 of human CS1 fused
      to amino acids
      149-224 of mouse CS1

<400> SEQUENCE: 2

Met Ala Gly Ser Pro Thr Cys Leu Thr Leu Ile Tyr Ile Leu Trp Gln
1               5                   10                  15

Leu Thr Gly Ser Ala Ala Ser Gly Pro Val Lys Glu Leu Val Gly Ser
            20                  25                  30

Val Gly Gly Ala Val Thr Phe Pro Leu Lys Ser Lys Val Lys Gln Val
        35                  40                  45

Asp Ser Ile Val Trp Thr Phe Asn Thr Thr Pro Leu Val Thr Ile Gln
50                  55                  60

Pro Glu Gly Gly Thr Ile Ile Val Thr Gln Asn Arg Asn Arg Glu Arg
65                  70                  75                  80

Val Asp Phe Pro Asp Gly Gly Tyr Ser Leu Lys Leu Ser Lys Leu Lys
                85                  90                  95

Lys Asn Asp Ser Gly Ile Tyr Tyr Val Gly Ile Tyr Ser Ser Ser Leu
            100                 105                 110

Gln Gln Pro Ser Thr Gln Glu Tyr Val Leu His Val Tyr Glu His Leu
        115                 120                 125

Ser Lys Pro Lys Val Thr Ile Asp Arg Gln Ser Asn Lys Asn Gly Thr
130                 135                 140

Cys Val Ile Asn Leu Thr Cys Ser Thr Asp Gln Asp Gly Glu Asn Val
145                 150                 155                 160

Thr Tyr Ser Trp Lys Ala Val Gly Gln Gly Asp Asn Gln Phe His Asp
                165                 170                 175

Gly Ala Thr Leu Ser Ile Ala Trp Arg Ser Gly Glu Lys Asp Gln Ala
            180                 185                 190

Leu Thr Cys Met Ala Arg Asn Pro Val Ser Asn Ser Phe Ser Thr Pro
        195                 200                 205

Val Phe Pro Gln Lys Leu Cys Glu Asp Ala Ala Thr Asp Leu Thr Ser
    210                 215                 220

Leu Arg Gly
225

<210> SEQ ID NO 3
<211> LENGTH: 227
<212> TYPE: PRT
<213> ORGANISM: Artificial
```

<220> FEATURE:
<223> OTHER INFORMATION: mu25/hu75: amino acids 1-67 of mouse CS1 fused
      to amino acids 68-227 of human CS1

<400> SEQUENCE: 3

Met Ala Arg Phe Ser Thr Tyr Ile Ile Phe Thr Ser Val Leu Cys Gln
1               5                   10                  15

Leu Thr Val Thr Ala Ala Ser Gly Thr Leu Lys Lys Val Ala Gly Ala
            20                  25                  30

Leu Asp Gly Ser Val Thr Phe Thr Leu Asn Ile Thr Glu Ile Lys Val
        35                  40                  45

Asp Tyr Val Val Trp Thr Phe Asn Thr Phe Phe Leu Ala Met Val Lys
    50                  55                  60

Lys Asp Gly Gly Thr Ile Ile Val Thr Gln Asn Arg Asn Arg Glu Arg
65                  70                  75                  80

Val Asp Phe Pro Asp Gly Gly Tyr Ser Leu Lys Leu Ser Lys Leu Lys
                85                  90                  95

Lys Asn Asp Ser Gly Ile Tyr Tyr Val Gly Ile Tyr Ser Ser Ser Leu
            100                 105                 110

Gln Gln Pro Ser Thr Gln Glu Tyr Val Leu His Val Tyr Glu His Leu
        115                 120                 125

Ser Lys Pro Lys Val Thr Met Gly Leu Gln Ser Asn Lys Asn Gly Thr
    130                 135                 140

Cys Val Thr Asn Leu Thr Cys Cys Met Glu His Gly Glu Glu Asp Val
145                 150                 155                 160

Ile Tyr Thr Trp Lys Ala Leu Gly Gln Ala Ala Asn Glu Ser His Asn
                165                 170                 175

Gly Ser Ile Leu Pro Ile Ser Trp Arg Trp Gly Glu Ser Asp Met Thr
            180                 185                 190

Phe Ile Cys Val Ala Arg Asn Pro Val Ser Arg Asn Phe Ser Ser Pro
        195                 200                 205

Ile Leu Ala Arg Lys Leu Cys Glu Gly Ala Ala Asp Asp Pro Asp Ser
    210                 215                 220

Ser Met Val
225

<210> SEQ ID NO 4
<211> LENGTH: 224
<212> TYPE: PRT
<213> ORGANISM: Artificial
<220> FEATURE:
<223> OTHER INFORMATION: mu75/hu25: amino acids 1-166 of mouse CS1
      fused to amino acids 170-227 of human CS1

<400> SEQUENCE: 4

Met Ala Arg Phe Ser Thr Tyr Ile Ile Phe Thr Ser Val Leu Cys Gln
1               5                   10                  15

Leu Thr Val Thr Ala Ala Ser Gly Thr Leu Lys Lys Val Ala Gly Ala
            20                  25                  30

Leu Asp Gly Ser Val Thr Phe Thr Leu Asn Ile Thr Glu Ile Lys Val
        35                  40                  45

Asp Tyr Val Val Trp Thr Phe Asn Thr Phe Phe Leu Ala Met Val Lys
    50                  55                  60

Lys Asp Gly Val Thr Ser Gln Ser Ser Asn Lys Glu Arg Ile Val Phe
65                  70                  75                  80

Pro Asp Gly Leu Tyr Ser Met Lys Leu Ser Gln Leu Lys Lys Asn Asp
                85                  90                  95

```
Ser Gly Ala Tyr Arg Ala Glu Ile Tyr Ser Thr Ser Ser Gln Ala Ser
                100                 105                 110

Leu Ile Gln Glu Tyr Val Leu His Val Tyr Lys His Leu Ser Arg Pro
        115                 120                 125

Lys Val Thr Ile Asp Arg Gln Ser Asn Lys Asn Gly Thr Cys Val Ile
    130                 135                 140

Asn Leu Thr Cys Ser Thr Asp Gln Asp Gly Asn Val Thr Tyr Ser
145                 150                 155                 160

Trp Lys Ala Val Gly Gln Ala Ala Asn Glu Ser His Asn Gly Ser Ile
                165                 170                 175

Leu Pro Ile Ser Trp Arg Trp Gly Glu Ser Asp Met Thr Phe Ile Cys
            180                 185                 190

Val Ala Arg Asn Pro Val Ser Arg Asn Phe Ser Ser Pro Ile Leu Ala
                195                 200                 205

Arg Lys Leu Cys Glu Gly Ala Ala Asp Asp Pro Asp Ser Ser Met Val
            210                 215                 220
```

<210> SEQ ID NO 5
<211> LENGTH: 119
<212> TYPE: PRT
<213> ORGANISM: Homo saiens

<400> SEQUENCE: 5

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Ala Pro Ser Leu
    50                  55                  60

Lys Asp Lys Phe Ile Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Asp Gly Asn Tyr Trp Tyr Phe Asp Val Trp Gly Gln Gly
            100                 105                 110

Thr Leu Val Thr Val Ser Ser
        115
```

<210> SEQ ID NO 6
<211> LENGTH: 107
<212> TYPE: PRT
<213> ORGANISM: Homo sapiens

<400> SEQUENCE: 6

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Asp Arg Phe Ser Gly
    50                  55                  60
```

```
Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Ser Ser Tyr Pro Tyr
                85                  90                  95

Thr Phe Gly Gln Gly Thr Lys Val Glu Ile Lys
                100             105
```

METHODS OF TREATING MULTIPLE MYELOMA USING COMBINATION THERAPIES BASED ON ANTI-CS1 ANTIBODIES

1. CROSS REFERENCE TO RELATED APPLICATIONS

This application claims benefit under 35 U.S.C. §119(e) to application Ser. Nos. 60/836,185, filed Aug. 7, 2006 and 60/944,262, filed Jun. 15, 2007, the contents of which are incorporated herein by reference.

2. BACKGROUND

Multiple myeloma ("MM") represents a malignant proliferation of plasma cells derived from a single clone. The terms multiple myeloma and myeloma are used interchangeably to refer to the same condition. The myeloma tumor, its products, and the host response to it result in a number of organ dysfunctions and symptoms of bone pain or fracture, renal failure, susceptibility to infection, anemia, hypocalcemia, and occasionally clotting abnormalities, neurologic symptoms and vascular manifestations of hyperviscosity. See D. Longo, in Harrison's Principles of Internal Medicine 14th Edition, p. 713 (McGraw-Hill, New York, 1998). No effective long-term treatment currently exists for MM. It is a malignant disease of plasma cells, manifested as hyperproteinemia, anemia, renal dysfunction, bone lesions, and immunodeficiency. MM is difficult to diagnose early because there may be no symptoms in the early stage. The disease has a progressive course with a median duration of survival of six months when no treatment is given. Systemic chemotherapy is the main treatment, and the current median of survival with chemotherapy is about three years, however fewer than 5% live longer than 10 years (See Anderson, K. et al., Annual Meeting Report 1999. Recent Advances in the Biology and Treatment of Multiple Myeloma (1999)).

While multiple myeloma is considered to be a drug-sensitive disease, almost all patients with MM who initially respond to chemotherapy eventually relapse (See Anderson, K. et al., Annual Meeting Report 1999. Recent Advances in the Biology and Treatment of Multiple Myeloma (1999)). Since the introduction of melphalan and prednisone therapy for MM, numerous multi-drug chemotherapies including Vinca alkaloid, anthracycline, and nitrosourea-based treatment have been tested (See Case, D C et al., (1977) Am. J. Med 63:897 903), but there has been little improvement in outcome over the past three decades (See Case, D C et al., (1977) Am. J. Med 63:897 903; Otsuki, T. et al, (2000) Cancer Res. 60:1). New methods of treatment, such as combination therapies utilizing monoclonal antibodies and therapeutic agents, are needed.

3. SUMMARY

Described herein are compositions and methods useful for exploiting the anti-tumor properties of anti-CS1 antibodies. Anti-CS1 antibodies that can be used in the methods and compositions are described in U.S. Patent Publication Nos. 2005/0025763 and 2006/0024296, the contents of which are incorporated herein by reference. The anti-CS1 antibodies target CS1 (CD2-subset1), which is also known as SLAMF7, CRACC, 19A, APEX-1, and FOAP12 (Genbank Accession Number NM_021181.3). CS1, is a glycoprotein that is highly expressed in bone marrow samples from patients diagnosed with MM. In both in vitro and in vivo studies, anti-CS1 antibodies exhibit significant anti-myeloma activity (see, e.g., U.S. Patent Publication Nos. 2005/0025763 and 2006/0024296, the contents of which are incorporated herein by reference). By way of example, but not limitation, the anti-CS1 antibody, HuLuc63 effectively mediates lysis of myeloma cells via antibody dependent cellular cytotoxicity (ADCC) (see, e.g., U.S. Patent Publication No. 2005/0025763, the content of which is incorporated herein by reference). In a myeloma mouse tumor model, treatment with HuLuc63 significantly reduced tumor mass by more than 50% (see, e.g., U.S. Patent Publication No. 2005/0025763, the content of which is incorporated herein by reference).

The present disclosure relates to compositions and methods for treating patients diagnosed with Monoclonal Gammopathy of Undetermined Significance (MGUS), smoldering myeloma, asymptomatic MM, and symptomatic MM, ranging from newly diagnosed to late stage relapsed/refractory. In particular, the methods relate to the administration of a pharmaceutical composition comprising an anti-CS1 antibody, such as HuLuc63, in combination with one or more therapeutic agents. The anti-CS1 antibody is typically administered in a first pharmaceutical composition as an intravenous infusion at doses ranging from 0.5 to 20 mg/kg, from once a week to once a month.

A second pharmaceutical composition comprising one or more therapeutic agents, such as bortezomib and lenalidomide, can be administered concurrently, prior to, or following administration of an anti-CS1 antibody. Depending on the agent, the composition can be administered orally, intravenously or subcutaneously. Therapeutic agents can be used at high dose rates, standard dose rates and at reduced dose rates.

In some embodiments, administration of the pharmaceutical compositions described herein increases the sensitivity of multiple myeloma cells to a therapeutic agent. By way of example, but not limitation, inclusion of an anti-CS1 antibody can enhance the activity of the therapeutic agent, such that lower doses can be used in the compositions and methods described herein.

In some embodiments, administration of the pharmaceutical compositions described herein elicits at least one of the beneficial responses as defined by the European Group for Blood and Marrow transplantation (EBMT). For example, administration of the pharmaceutical compositions described herein can result in a complete response, partial response, minimal response, no change, or plateau.

4. BRIEF DESCRIPTION OF THE FIGURES

5. DETAILED DESCRIPTION

Figure 1A:
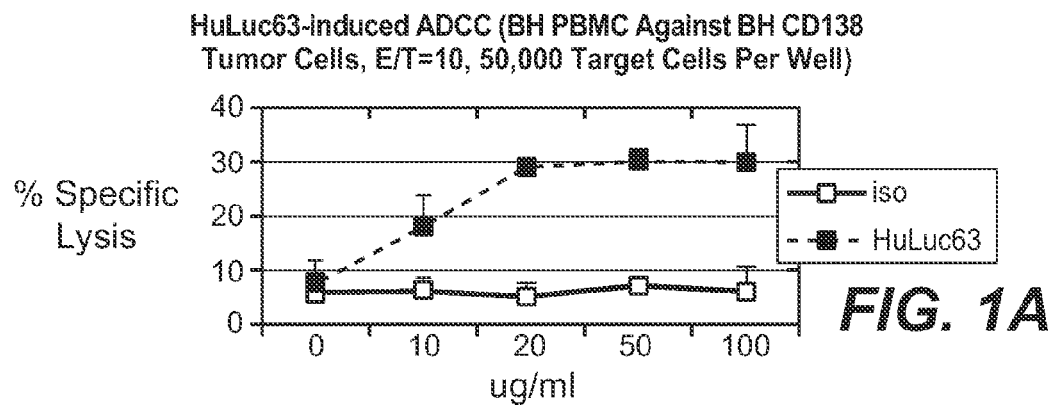
FIGS. 1A-1C depict autologous ADCC-mediated lysis of MM cells treated with HuLuc63.
Figure 1B:
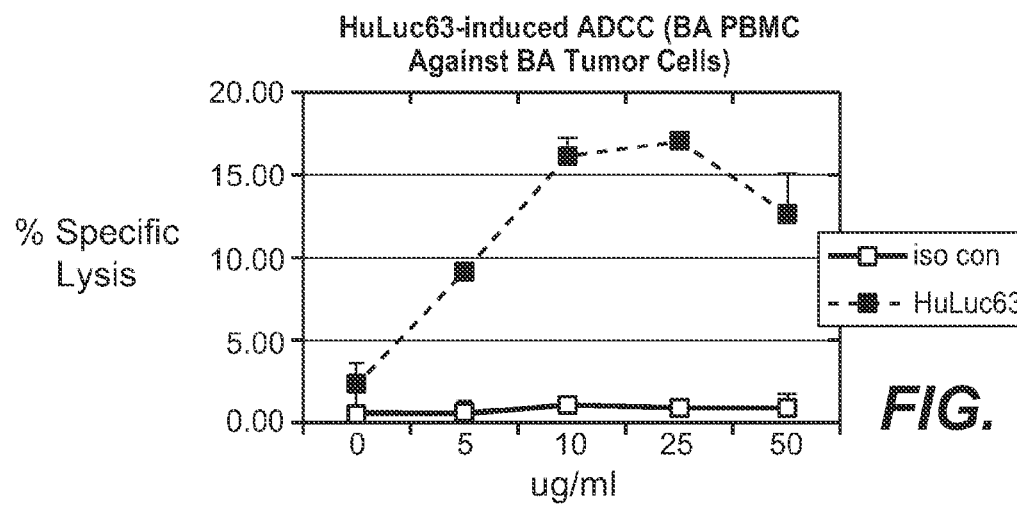
Figure 1C:
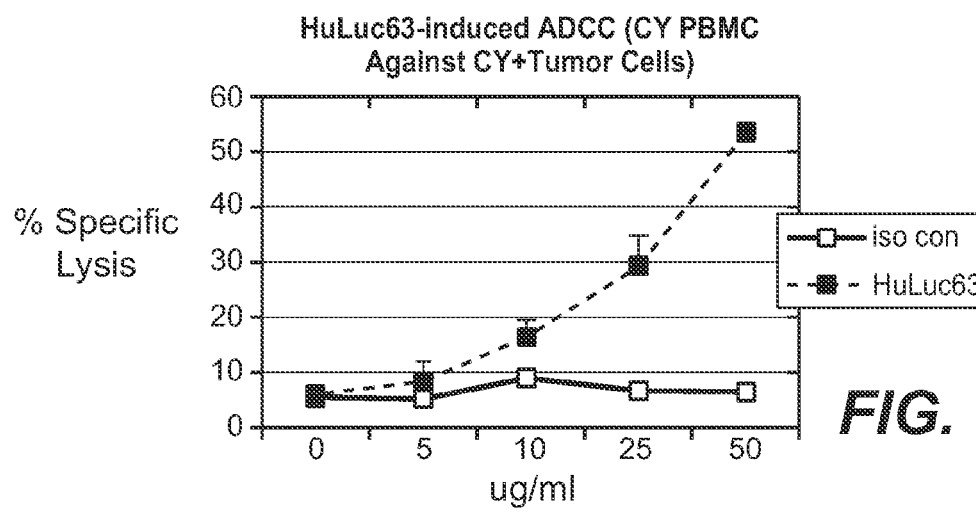

The compositions described herein combine anti-CS1 antibodies with one or more therapeutic agents at specific doses to potentiate or complement the anti-myeloma activities of the other. Examples of suitable anti-CS1 antibodies include, but are not limited to, isolated antibodies that bind one or more of the three epitope clusters identified on CS1 and monoclonal antibodies produced by the hybridoma cell lines: Luc2, Luc3, Luc15, Luc22, Luc23, Luc29, Luc32, Luc34, Luc35, Luc37, Luc38, Luc39, Luc56, Luc60, Luc63, Luc69, LucX.1, LucX.2 or Luc90. These monoclonal antibodies are named as the antibodies: Luc2, Luc3, Luc15, Luc22, Luc23, Luc29, Luc32, Luc34, Luc35, Luc37, Luc38, Luc39, Luc56, Luc60, Luc63, Luc69, LucX and Luc90, respectively, hereafter. Humanized versions are denoted by the prefix "hu" (see, e.g., U.S. Patent Publication Nos. 2005/0025763 and 2006/0024296, the contents of which are incorporated herein by reference).

In some embodiments, suitable anti-CS1 antibodies include isolated antibodies that bind one or more of the three epitope clusters identified on CS1 (SEQ ID NO: 1, Table 1 below; see, e.g., U.S. Patent Publication No. 2006/0024296, the content of which is incorporated herein by reference). As disclosed in U.S. Patent Publication No. 2006/0024296 and shown below in Table 1, the CS1 antibody binding sites have been grouped into 3 epitope clusters:

(1) the epitope defined by Luc90, which binds to hu50/mu50 (SEQ ID NO: 2). This epitope covers from about amino acid residue 23 to about amino acid residue 151 of human CS1. This epitope is resided within the domain 1 (V domain) of the extracellular domain. This epitope is also recognized by Luc34, LucX (including LucX.1 and LucX.2) and Luc69.

(2) the epitope defined by Luc38, which binds to mu25/hu75 (SEQ ID NO: 3) and hu50/mu50 (SEQ ID NO: 81). This epitope likely covers from about amino acid residue 68 to about amino acid residue 151 of human CS1. This epitope is also recognized by Luc5.

(3) the epitope defined by Luc 63, which binds to mu75/hu25 (SEQ ID NO: 4). This epitope covers from about amino acid residue 170 to about amino acid residue 227 of human CS1. This epitope is resided within domain 2 (C2 domain) of human CS1. This epitope is also recognized by Luc4, Luc12, Luc23, Luc29, Luc32 and Luc37.

The methods and pharmaceutical compositions are addressed in more detail below, but typically include at least one anti-CS1 antibody as described above. In some embodiments, the pharmaceutical compositions include the anti-CS1 antibody HuLuc63. HuLuc63 is a humanized recombinant monoclonal IgG1 antibody directed to human CS1. The amino acid sequence for the heavy chain variable region (SEQ ID NO: 5) and the light chain variable region (SEQ ID NO: 6) for HuLuc63 is disclosed in U.S. Patent Publication No. 2005/0025763, the content of which is incorporated herein by reference, and in Table 1.

TABLE 1

| SEQ ID NO: | Amino Acid Sequence |
|---|---|
| SEQ ID NO: 1 | Met Ala Gly Ser Pro Thr Cys Leu Thr Leu Ile Tyr Ile Leu Trp Gln Leu Thr Gly Ser Ala Ala Ser Gly Pro Val Lys Glu Leu Val Gly Ser Val Gly Gly Ala Val Thr Phe Pro Leu Lys Ser Lys Val Lys Gln Val Asp Ser Ile Val Trp Thr Phe Asn Thr Thr Pro Leu Val Thr Ile Gln Pro Glu Gly Gly Thr Ile Ile Val Thr Gln Asn Arg Asn Arg Glu Arg Val Asp Phe Pro Asp Gly Gly Tyr Ser Leu Lys Leu Ser Lys Leu Lys Lys Asn Asp Ser Gly Ile Tyr Tyr Val Gly Ile Tyr Ser Ser Ser Leu Gln Gln Pro Ser Thr Gln Glu Tyr Val Leu His Val Tyr Glu His Leu Ser Lys Pro Lys Val Thr Met Gly Leu Gln Ser Asn Lys Asn Gly |

TABLE 1-continued

| SEQ ID NO: | Amino Acid Sequence |
|---|---|
| | Thr Cys Val Thr Asn Leu Thr Cys Cys Met Glu His Gly Glu Glu Asp Val Ile Tyr Thr Trp Lys Ala Leu Gly Gln Ala Ala Asn Glu Ser His Asn Gly Ser Ile Leu Pro Ile Ser Trp Arg Trp Gly Glu Ser Asp Met Thr Phe Ile Cys Val Ala Arg Asn Pro Val Ser Arg Asn Phe Ser Ser Pro Ile Leu Ala Arg Lys Leu Cys Glu Gly Ala Ala Asp Asp Pro Asp Ser Ser Met Val Leu Leu Cys Leu Leu Leu Val Pro Leu Leu Leu Ser Leu Phe Val Leu Gly Leu Phe Leu Trp Phe Leu Lys Arg Glu Arg Gln Glu Glu Tyr Ile Glu Glu Lys Lys Arg Val Asp Ile Cys Arg Glu Thr Pro Asn Ile Cys Pro His Ser Gly Glu Asn Thr Glu Tyr Asp Thr Ile Pro His Thr Asn Arg Thr Ile Leu Lys Glu Asp Pro Ala Asn Thr Val Tyr Ser Thr Val Glu Ile Pro Lys Lys Met Glu Asn Pro His Ser Leu Leu Thr Met Pro Asp Thr Pro Arg Leu Phe Ala Tyr Glu Asn Val Ile |
| SEQ ID NO: 2 | Met Ala Gly Ser Pro Thr Cys Leu Thr Leu Ile Tyr Ile Leu Trp Gln Leu Thr Gly Ser Ala Ala Ser Gly Pro Val Lys Glu Leu Val Gly Ser Val Gly Gly Ala Val Thr Phe Pro Leu Lys Ser Lys Val Lys Gln Val Asp Ser Ile Val Trp Thr Phe Asn Thr Thr Pro Leu Val Thr Ile Gln Pro Glu Gly Gly Thr Ile Ile Val Thr Gln Asn Arg Asn Arg Glu Arg Val Asp Phe Pro Asp Gly Gly Tyr Ser Leu Lys Leu Ser Lys Leu Lys Lys Asn Asp Ser Gly Ile Tyr Tyr Val Gly Ile Tyr Ser Ser Ser Leu Gln Gln Pro Ser Thr Gln Glu Tyr Val Leu His Val Tyr Glu His Leu Ser Lys Pro Lys Val Thr Ile Asp Arg Gln Ser Asn Lys Asn Gly Thr Cys Val Ile Asn Leu Thr Cys Ser Thr Asp Gln Asp Gly Glu Asn Val Thr Tyr Ser Trp Lys Ala Val Gly Gln Gly Asp Asn Gln Phe His Ser Gly Ala Thr Leu Ser Ile Ala Trp Arg Ser Gly Glu Lys Asp Gln Ala Leu Thr Cys Met Ala Arg Asn Pro Val Ser Asn Ser Phe Ser Thr Pro Val Phe Pro Gln Lys Leu Cys Glu Asp Ala Ala Thr Asp Leu Thr Ser Leu Arg Gly |
| SEQ ID NO: 3 | Met Ala Arg Phe Ser Thr Tyr Ile Ile Phe Thr Ser Val Leu Cys Gln Leu Thr Val Thr Ala Ala Ser Gly Thr Leu Lys Lys Val Ala Gly Ala Leu Asp Gly Ser Val Thr Phe Thr Leu Asn Ile Thr Glu Ile Lys Val Asp Tyr Val Val Trp Thr Phe Asn Thr Phe Phe Leu Ala Met Val Lys Lys Asp Gly Gly Thr Ile Ile Val Thr Gln Asn Arg Asn Arg Glu Arg Val Asp Phe Pro Asp Gly Gly Tyr Ser Leu Lys Leu Ser Lys Leu Lys Lys Asn Asp Ser Gly Ile Tyr Tyr Val Gly Ile Tyr Ser Ser Ser Leu Gln Gln Pro Ser Thr Gln Glu Tyr Val Leu His Val Tyr Glu His Leu Ser Lys Pro Lys Val Thr Met Gly Leu Gln Ser Asn Lys Asn Gly Thr Cys Val Thr Asn Leu Thr Cys Cys Met Glu His Gly Glu Glu Asp Val Ile Tyr Thr Trp Lys Ala Leu Gly Gln Ala Ala Asn Glu Ser His Asn Gly Ser Ile Leu Pro Ile Ser Trp Arg Trp Gly Glu Ser Asp Met Thr Phe Ile Cys Val Ala Arg Asn Pro Val Ser Arg Asn Phe Ser Ser Pro Ile Leu Ala Arg Lys Leu Cys Glu Gly Ala Ala Asp Asp Pro Asp Ser Ser Met Val |
| SEQ ID NO: 4 | Met Ala Arg Phe Ser Thr Tyr Ile Ile Phe Thr Ser Val Leu Cys Gln Leu Thr Val Thr Ala Ala Ser Gly Thr Leu Lys Lys Val Ala Gly Ala Leu Asp Gly Ser Val Thr Phe Thr Leu Asn Ile Thr Glu Ile Lys Val Asp Tyr Val Val Trp Thr Phe Asn Thr Phe Phe Leu Ala Met Val Lys Lys Asp Gly Val Thr Ser Gln Ser Ser Asn Lys Glu Arg Ile Val Phe Pro Asp Gly Leu Tyr Ser Met Lys Leu Ser Gln Leu Lys Lys Asn Asp Ser Gly Ala Tyr Arg Ala Glu Ile Tyr Ser Thr Ser Ser Gln Ala Ser Leu Ile Gln Glu Tyr Val Leu His Val Tyr Lys His Leu Ser Arg Pro Lys Val Thr Ile Asp Arg Gln Ser Asn Lys Asn Gly Thr Cys Val Ile Asn Leu Thr Cys Ser Thr Asp Gln Asp Gly |

TABLE 1-continued

| SEQ ID NO: | Amino Acid Sequence |
|---|---|
| | Glu Asn Val Thr Tyr Ser Trp Lys Ala Val Gly |
| | Gln Ala Ala Asn Glu Ser His Asn Gly Ser Ile |
| | Leu Pro Ile Ser Trp Arg Trp Gly Glu Ser Asp |
| | Met Thr Phe Ile Cys Val Ala Arg Asn Pro Val |
| | Ser Arg Asn Phe Ser Ser Pro Ile Leu Ala Arg |
| | Lys Leu Cys Glu Gly Ala Ala Asp Asp Pro Asp |
| | Ser Ser Met Val |
| SEQ ID NO: 5 | Glu Val Gln Leu Val Glu Ser Gly Gly Gly Leu Val Gln Pro Gly Gly Ser Leu Arg Leu Ser Cys Ala Ala Ser Gly Phe Asp Phe Ser Arg Tyr Trp Met Ser Trp Val Arg Gln Ala Pro Gly Lys Gly Leu Glu Trp Ile Gly Glu Ile Asn Pro Asp Ser Ser Thr Ile Asn Tyr Ala Pro Ser Leu Lys Asp Lys Phe Ile Ile Ser Arg Asp Asn Ala Lys Asn Ser Leu Tyr Leu Gln Met Asn Ser Leu Arg Ala Glu Asp Thr Ala Val Tyr Tyr Cys Ala Arg Pro Asp Gly Asn Tyr Trp Tyr Phe Asp Val Trp Gly Gln Gly Thr Leu Val Thr Val Ser Ser |
| SEQ ID NO: 6 | Asp Ile Gln Met Thr Gln Ser Pro Ser Ser Leu Ser Ala Ser Val Gly Asp Arg Val Thr Ile Thr Cys Lys Ala Ser Gln Asp Val Gly Ile Ala Val Ala Trp Tyr Gln Gln Lys Pro Gly Lys Val Pro Lys Leu Leu Ile Tyr Trp Ala Ser Thr Arg His Thr Gly Val Pro Asp Arg Phe Ser Gly Ser Gly Ser Gly Thr Asp Phe Thr Leu Thr Ile Ser Ser Leu Gln Pro Glu Asp Val Ala Thr Tyr Tyr Cys Gln Gln Tyr Ser Ser Tyr Pro Tyr Thr Phe Gly Gln Gly Thr Lys Val Glu Ile Lys |

At some doses, additive effects are seen; at other doses, synergistic effects are seen. In some embodiments, the synergistic effect permits one or more therapeutic agents to be administered in combination with one or more anti-CS1 antibodies at a reduced dosage, while retaining efficacy. Given that the side effects associated with the use of these agents are dose-dependent, use of the compositions and methods described herein can reduce the deleterious side effects observed in conventional and novel treatment regimens used to treat MM when these agents are administered at their recommended dosages.

In other embodiments, the synergistic effect permits one or more therapeutic agents to be administered in combination with one or more anti-CS1 antibodies at the approved dosage, but with greater than the expected efficacy.

The compositions can be administered for the treatment of Monoclonal Gammopathy of Undetermined Significance (MGUS), smoldering myeloma, asymptomatic MM, and symptomatic MM, ranging from newly diagnosed to late stage relapsed/refractory. Typically, administration of the compositions results in a reduction in M-protein in serum or urine such that a plateau, no change, minimal, partial or complete response is observed as defined by the European Group for Blood and Marrow transplantation (EBMT).

5.2 Pharmaceutical Compositions

Provided herein are pharmaceutical compositions that are beneficial in reducing tumor mass and/or regressing tumor growth, in patients diagnosed with multiple myeloma. The components of the pharmaceutical compositions are addressed in more detail below, but typically include an anti-CS1 antibody, such as HuLuc63 and one or more therapeutic agents. In some embodiments, the various components of the compositions are provided separately. For example, an anti-CS1 antibody can be provided in a first pharmaceutical composition, and a therapeutic agent provided in a second composition. When the composition comprises two or more therapeutic agents, an anti-CS1 antibody can be provided in a first pharmaceutical composition, one therapeutic agent can be provided in a second composition and the other therapeutic agent can be provided in a third composition. In other embodiments, an anti-CS1 antibody can be provided in one pharmaceutical composition and the therapeutic agents can be combined and provided in a second pharmaceutical composition. In still other embodiments, one composition, comprising an anti-CS1 antibody combined with one or more therapeutic agents can be provided.

In typical embodiments, an anti-CS1 antibody is present in a pharmaceutical composition at a concentration sufficient to permit intravenous administration at 0.5 mg/kg to 20 mg/kg. In some embodiments, the concentration of HuLuc63 suitable for use in the compositions and methods described herein includes, but is not limited to, at least about 0.5 mg/kg, at least about 0.75 mg/kg, at least about 1 mg/kg, at least about 2 mg/kg, at least about 2.5 mg/kg, at least about 3 mg/kg, at least about 4 mg/kg, at least about 5 mg/kg, at least about 6 mg/kg, at least about 7 mg/kg, at least about 8 mg/kg, at least about 9 mg/kg, at least about 10 mg/kg, at least about 11 mg/kg, at least about 12 mg/kg, at least about 13 mg/kg, at least about 14 mg/kg, at least about 15 mg/kg, at least about 16 mg/kg, at least about 17 mg/kg, at least about 18 mg/kg, at least about 19 mg/kg, and at least about 20 mg/kg.

The anti-CS1 antibodies can be administered in single or multiple dose regimens. Generally, an anti-CS1 antibody is administered over a period of time from about 1 to about 24 hours, but is typically administered over a period of about 1 to 2 hours. Dosages can be repeated from about 1 to about 4 weeks or more, for a total of 4 or more doses. Typically, dosages are repeated once every week, once every other week, or once a month, for a minimum of 4 doses to a maximum of 52 doses.

Determination of the effective dosage, total number of doses, and length of treatment with an anti-CS1 antibody is well within the capabilities of those skilled in the art, and can be determined using a standard dose escalation study to identify the maximum tolerated dose (MTD) (see, e.g., Richardson et al., 2002, Blood, 100(9):3063-3067, the content of which is incorporated herein by reference).

In some embodiments, one or more therapeutic agents are administered in combination with an anti-CS1 antibody. The agents can be administered concurrently, prior to, or following administration of an anti-CS1 antibody.

In some embodiments, an anti-CS1 antibody is administered prior to the administration of the therapeutic agents. For example, an anti-CS1 antibody can be administered approximately 0 to 60 days prior to the administration of the therapeutic agents. In some embodiments, an anti-CS1 antibody, such as HuLuc63, is administered from about 30 minutes to about 1 hour prior to the administration of the therapeutic agents, or from about 1 hour to about 2 hours prior to the administration of the therapeutic agents, or from about 2 hours to about 4 hours prior to the administration of the therapeutic agents, or from about 4 hours to about 6 hours prior to the administration of the therapeutic agents, or from about 6 hours to about 8 hours prior to the administration of the therapeutic agents, or from about 8 hours to about 16 hours prior to the administration of the therapeutic agents, or from about 16 hours to 1 day prior to the administration of the therapeutic agents, or from about 1 to 5 days prior to the administration of the therapeutic agents, or from about 5 to 10 days prior to the administration of the therapeutic agents, or from about 10 to 15 days prior to the administration of the therapeutic agents, or from about 15 to 20 days prior to the administration of the therapeutic agents, or from about 20 to 30 days prior to the administration of the therapeutic agents, or from about 30 to 40 days prior to the administration of the therapeutic agents, and from about 40 to 50 days prior to the administration of the therapeutic agents, or from about 50 to 60 days prior to the administration of the therapeutic agents.

In some embodiments, an anti-CS1 antibody is administered concurrently with the administration of the therapeutic agents.

In some embodiments, an anti-CS1 antibody is administered following the administration of the therapeutic agents. For example, an anti-CS1 antibody, such as HuLuc63, can be administered approximately 0 to 60 days after the administration of the therapeutic agents. In some embodiments, HuLuc63 is administered from about 30 minutes to about 1 hour following the administration of the therapeutic agents, or from about 1 hour to about 2 hours following the administration of the therapeutic agents, or from about 2 hours to about 4 hours following the administration of the therapeutic agents, or from about 4 hours to about 6 hours following the administration of the therapeutic agents, or from about 6 hours to about 8 hours following the administration of the therapeutic agents, or from about 8 hours to about 16 hours following the administration of the therapeutic agents, or from about 16 hours to 1 day following the administration of the therapeutic agents, or from about 1 to 5 days following the administration of the therapeutic agents, or from about 5 to 10 days following the administration of the therapeutic agents, or from about 10 to 15 days following the administration of the therapeutic agents, or from about 15 to 20 days following the administration of the therapeutic agents, or from about 20 to 30 days following the administration of the therapeutic agents, or from about 30 to 40 days following the administration of the therapeutic agents, and from about 40 to 50 days following the administration of the therapeutic agents, or from about 50 to 60 days following the administration of the therapeutic agents.

The therapeutic agents can be administered in any manner found appropriate by a clinician and are typically provided in generally accepted efficacious dose ranges, such as those described in the Physician Desk Reference, 56th Ed. (2002), Publisher Medical Economics, New Jersey. In other embodiments, a standard dose escalation can be performed to identify the maximum tolerated dose (MTD) (see, e.g., Richardson, et al. 2002, Blood, 100(9):3063-3067, the content of which is incorporated herein by reference).

In some embodiments, doses less than the generally accepted efficacious dose of a therapeutic agent can be used. For example, in various embodiments, the composition comprises a dosage that is less than about 10% to 75% of the generally accepted efficacious dose range. In some embodiments, at least about 10% or less of the generally accepted efficacious dose range is used, at least about 15% or less, at least about 25%, at least about 30% or less, at least about 40% or less, at least about 50% or less, at least about 60% or less, at least about 75% or less, and at least about 90%.

The therapeutic agents can be administered singly or sequentially, or in a cocktail with other therapeutic agents, as described below. The therapeutic agents can be administered orally, intravenously, systemically by injection intramuscularly, subcutaneously, intrathecally or intraperitoneally.

Examples of therapeutic agents that can be used in the compositions described herein include, but are not limited to, dexamethasone, thalidomide, melphalan, prednisone, doxorubicin, doxorubicin HCL liposome injection, bortezomib, lenalidomide, and/or combinations thereof.

Accordingly, in some embodiments, two pharmaceutical compositions are provided: a first comprising a therapeutically effective amount of an anti-CS1 antibody, such as HuLuc63 and a second comprising a therapeutically effective amount of lenalidomide.

In some embodiments, two pharmaceutical compositions are provided: a first comprising a therapeutically effective amount of an anti-CS1 antibody, such as HuLuc63, and a second comprising a therapeutically effective amount of bortezomib.

In some embodiments, at least two pharmaceutical compositions are provided: a first comprising a therapeutically effective amount of an anti-CS1 antibody, such as HuLuc63 and a second comprising a therapeutically effective amount of lenalidomide and a therapeutically effective amount of bortezomib. In some embodiments, lenalidomide and bortezomib are provided separately, such that a total of three pharmaceutical compositions are provided: a first comprising an anti-CS1 antibody, such as HuLuc63, a second comprising lenalidomide, and a third comprising bortezomib.

In some embodiments, at least two pharmaceutical compositions are provided: a first comprising a therapeutically effective amount of an anti-CS1 antibody, such as HuLuc63 and a second comprising a therapeutically effective amount of lenalidomide and dexamethasone. In some embodiments, lenalidomide and dexamethasone are provided separately, such that a total of three pharmaceutical compositions are provided: a first comprising an anti-CS1 antibody, such as HuLuc63, a second comprising lenalidomide, and a third comprising dexamethasone.

In some embodiments at least two pharmaceutical compositions are provided: a first comprising a therapeutically effective amount of an anti-CS1 antibody, such as HuLuc63 and a second comprising a therapeutically effective amount of bortezomib and dexamethasone. In some embodiments, bortezomib and dexamethasone are provided separately, such that a total of three pharmaceutical compositions are provided: a first comprising an anti-CS1 antibody, such as HuLuc63, a second comprising bortezomib, and a third comprising dexamethasone.

In some embodiments, at least two pharmaceutical compositions are provided: a first comprising a therapeutically effective amount of an anti-CS1 antibody, such as HuLuc63, and a second comprising therapeutically effective amount of lenalidomide, bortezomib, and dexamethasone. In some embodiments, lenalidomide, bortezomib, and dexamethasone are provided separately. Provided that the agents retain their efficacy, compositions comprising other combinations can be prepared, depending in part, on dosage, route of administration, and whether the agents are provided in a solid, semi-solid or liquid form. For example, a total of three compositions can be made: a first comprising a therapeutically effective amount of an anti-CS1 antibody, such as HuLuc63, a second comprising dexamethasone, and a third comprising lenalidomide and bortezomib.

In some embodiments, at least two pharmaceutical compositions are provided: a first comprising a therapeutically effective amount of an anti-CS1 antibody, such as HuLuc63, and a second comprising a therapeutically effective amount of bortezomib and optionally can comprise one or more of the following agents: thalidomide, dexamethasone, melphalan, doxorubicin, doxorubicin HCl liposome injection, and/or prednisone. Provided that the agents retain their efficacy, compositions comprising various combinations of thalidomide, dexamethasone, melphalan, doxorubicin, doxorubicin HCl liposome injection, and prednisone can be prepared depending in part, on dosage, route of administration, and whether the agents are provided in a solid, semi-solid or liquid form.

The pharmaceutical compositions can exist as a solid, semi-solid, or liquid (e.g., suspensions or aerosols) dosage form. Typically, the compositions are administered in unit dosage forms suitable for single administration of precise dosage amounts. For example, anti-CS1 antibodies can be packaged in dosages ranging from about 1 to 1000 mg. In some embodiments, anti-CS1 antibodies can be packaged in a dosage at least about 1 mg, at least about 10 mg, at least about 20 mg, at least about 50 mg, at least about 100 mg, at least about 200 mg, at least about 300 mg, at least about 400 mg, at least about 500 mg, at least about 750 mg, at least about 1000 mg.

The compositions can also include, depending on the formulation desired, pharmaceutically-acceptable, nontoxic carriers or diluents, which are defined as vehicles commonly used to formulate pharmaceutical compositions for animal or human administration. The diluent is selected so as not to affect the biological activity of the combination. Examples of such diluents are distilled water, physiological saline, Ringer's solution, dextrose solution, and Hank's solution.

In addition, the pharmaceutical composition or formulation can also include other carriers, adjuvants, or nontoxic, non-therapeutic, nonimmunogenic stabilizers and the like. Effective amounts of such diluent or carrier will be those amounts that are effective to obtain a pharmaceutically acceptable formulation in terms of solubility of components, or biological activity.

5.3 Methods

The pharmaceutical compositions described herein find use in treating MM. Typically, the compositions can be used to treat Monoclonal Gammopathy of Undetermined Significance (MGUS), smoldering myeloma, asymptomatic MM, and symptomatic MM, ranging from newly diagnosed to late stage relapsed/refractory.

The compositions can be combined with other treatment strategies, i.e., autologous stem cell transplantation and allogeneic effector cell transplantation, to develop an effective treatment strategy based on the stage of myeloma being treated (see, e.g., Multiple Myeloma Research Foundation, Multiple Myeloma: Stem Cell Transplantation 1-30 (2004); U.S. Pat. Nos. 6,143,292, and 5,928,639, Igarashi, et al. Blood 2004, 104(1): 170-177, Maloney, et al. 2003, Blood, 102(9): 3447-3454, Badros, et al. 2002, J Clin Oncol., 20:1295-1303, Tricot, et al. 1996, Blood, 87(3):1196-1198; the contents of which are incorporated herein by reference).

The staging system most widely used since 1975 has been the Durie-Salmon system, in which the clinical stage of disease (Stage I, II, or III) is based on four measurements (see, e.g., Durie and Salmon, 1975, Cancer, 36:842-854). These four measurements are: (1) levels of monoclonal (M) protein (also known as paraprotein) in the serum and/or the urine; (2) the number of lytic bone lesions; (3) hemoglobin values; and, (4) serum calcium levels. These three stages can be further divided according to renal function, classified as A (relatively normal renal function, serum creatinine value<2.0 mg/dL) and B (abnormal renal function, creatinine value≥2.0 mg/dL). A new, simpler alternative is the International Staging System (ISS) (see, e.g., Greipp et al., 2003, "Development of an international prognostic index (IPI) for myeloma: report of the international myeloma working group", The Hematology). The ISS is based on the assessment of two blood test results, beta$_2$-microglobulin ($\beta_2$-M) and albumin, which separates patients into three prognostic groups irrespective of type of therapy.

Administration of the pharmaceutical compositions at selected dosage ranges and routes typically elicits a beneficial response as defined by the European Group for Blood and Marrow transplantation (EBMT). Table 2 lists the EBMT criteria for response.

TABLE 2

| EBMT/IBMTR/ABMTR[1] Criteria for Response | |
|---|---|
| Complete Response | No M-protein detected in serum or urine by immunofixation for a minimum of 6 weeks and fewer than 5% plasma cells in bone marrow |
| Partial Response | >50% reduction in serum M-protein level and/or 90% reduction in urine free light chain excretion or reduction to <200 mg/24 hrs for 6 weeks[2] |
| Minimal Response | 25-49% reduction in serum M-protein level and/or 50-89% reduction in urine free light chain excretion which still exceeds 200 mg/24 hrs for 6 weeks[3] |
| No Change | Not meeting the criteria or either minimal response or progressive disease |
| Plateau | No evidence of continuing myeloma-related organ or tissue damage, <25% change in M-protein levels and light chain excretion for 3 months |
| Progressive Disease | Myeloma-related organ or tissue damage continuing despite therapy or its reappearance in plateau phase, >25% increase in serum M-protein level (>5 g/L) and/or >25% increase in urine M-protein level (>200 mg/24 hrs) and/or >25% increase in bone marrow plasma cells (at least 10% in absolute terms)[2] |
| Relapse | Reappearance of disease in patients previously in complete response, including detection of paraprotein by immunofixation |

[1]EBMT: European Group for Blood and Marrow transplantation; IBMTR: International Bone Marrow Transplant Registry; ABMTR: Autologous Blood and Marrow Transplant Registry.

Additional criteria that can be used to measure the outcome of a treatment include "near complete response" and "very good partial response". A "near complete response" is defined as the criteria for a "complete response" (CR), but with a positive immunofixation test. A "very good partial response" is defined as a greater than 90% decrease in M protein (see, e.g., Multiple Myeloma Research Foundation, Multiple Myeloma: Treatment Overview 9 (2005)).

The degree to which administration of the compositions elicits a response in an individual clinically manifesting at least one symptom associated with MM, depends in part, on the severity of disease, e.g., Stage I, II, or III, and in part, on whether the patient is newly diagnosed or has late stage refractory MM. Thus, in some embodiments, administration of the pharmaceutical composition elicits a complete response.

In other embodiments, administration of the pharmaceutical composition elicits a very good partial response or a partial response.

In other embodiments, administration of the pharmaceutical composition elicits a minimal response.

In other embodiments, administration of the pharmaceutical composition prevents the disease from progressing, resulting in a response classified as "no change" or "plateau" by the EBMT.

Routes of administration and dosage ranges for compositions comprising an anti-CS1 antibody and one or more therapeutic agents for treating individuals diagnosed with MM, can be determined using art-standard techniques, such as a standard dose escalation study to identify the MTD (see, e.g., Richardson, et al. 2002, Blood, 100(9):3063-3067, the content of which is incorporated herein by reference).

Typically, anti-CS1 antibodies are administered intravenously. Administration of the other therapeutic agents described herein can be by any means known in the art. Such means include oral, rectal, nasal, topical (including buccal and sublingual) or parenteral (including subcutaneous, intramuscular, intravenous and intradermal) administration and will depend in part, on the available dosage form. For example, therapeutic agents that are available in a pill or capsule format typically are administered orally. However, oral administration generally requires administration of a higher dose than does intravenous administration. Determination of the actual route of administration that is best in a particular case is well within the capabilities of those skilled in the art, and in part, will depend on the dose needed versus the number of times per month administration is required.

Factors affecting the selected dosage of an anti-CS1 antibody and the therapeutic agents used in the compositions and methods described herein, include, but are not limited to, the type of agent, the age, weight, and clinical condition of the recipient patient, and the experience and judgment of the clinician or practitioner administering the therapy. Generally, the selected dosage should be sufficient to result in no change, but preferably results in at least a minimal change. An effective amount of a pharmaceutical agent is that which provides an objectively identifiable response, e.g., minimal, partial, or complete, as noted by the clinician or other qualified observer, and as defined by the EBMT.

Generally, an anti-CS1 antibody, such as HuLuc63, is administered as a separate composition from the composition(s) comprising the therapeutic agents. As discussed above, the therapeutic agents can each be administered as a separate composition, or combined in a cocktail and administered as a single combined composition. In some embodiments, the compositions comprising an anti-CS1 antibody and one or more therapeutic agents are administered concurrently. In other embodiments, an anti-CS1 antibody can be administered prior to the administration of composition(s) comprising the therapeutic agent(s). In yet other embodiments, an anti-CS1 antibody is administered following the administration of composition(s) comprising the therapeutic agent(s).

In those embodiments in which an anti-CS1 antibody is administered prior to or following the administration of the therapeutic agents, determination of the duration between the administration of an anti-CS1 antibody and administration of the agents is well within the capabilities of those skilled in the art, and in part, will depend on the dose needed versus the number of times per month administration is required.

Doses of anti-CS1 antibodies used in the methods described herein typically range between 0.5 mg/kg to 20 mg/kg. Optimal doses for the therapeutic agents are the generally accepted efficacious doses, such as those described in the Physician Desk Reference, 56th Ed. (2002), Publisher Medical Economics, New Jersey. Optimal doses for agents not described in the Physician Desk Reference can be determined using a standard dose escalation study to identify the MTD (see, e.g., Richardson, et al. 2002, Blood, 100(9):3063-3067, the contents of which are incorporated herein by reference).

In some embodiments, an anti-CS1 antibody is present in a pharmaceutical composition at a concentration, or in a weight/volume percentage, or in a weight amount, suitable for intravenous administration at a dosage rate at least about 0.5 mg/kg, at least about 0.75 mg/kg, at least about 1 mg/kg, at least about 2 mg/kg, at least about 2.5 mg/kg, at least about 3 mg/kg, at least about 4 mg/kg, at least about 5 mg/kg, at least about 6 mg/kg, at least about 7 mg/kg, at least about 8 mg/kg, at least about 9 mg/kg, at least about 10 mg/kg, at least about 11 mg/kg, at least about 12 mg/kg, at least about 13 mg/kg, at least about 14 mg/kg, at least about 15 mg/kg, at least about 16 mg/kg, at least about 17 mg/kg, at least about 18 mg/kg, at least about 19 mg/kg, and at least about 20 mg/kg.

6. EXAMPLES

Example 1

HuLuc63 in Combination with Lenalidomide

Lenalidomide is the first of a new class of oral cancer drugs called IMiDs®. These immunomodulatory derivatives are chemically similar to thalidomide but are more potent and have a different side effect profile than thalidomide. They have multiple mechanisms of action that affect both the cancer cell and its microenvironment. Lenalidomide has been shown to induce immune responses, enhance activity of immune cells, and inhibit inflammation. For example, lenalidomide may enhance the activation of T cells and NK cells, induce production of interleukin 2 and inhibit pro-inflammatory cytokines such as tumor necrosis factor-alpha and interleukin 1-beta. Currently lenalidomide in combination with dexamethasone is approved for $2^{nd}$ line therapy of multiple myeloma.

In vitro ADCC Assay: Methods and Results

ADCC was measured by calcein-AM release assay, with sensitivity similar to traditional $Cr^{51}$ assay, as described previously. After informed consent, peripheral blood mononuclear cells (PBMCs) including natural killer (NK) effector cells were isolated from leukopheresis products of normal donors or peripheral blood from MM patients. Increasing concentrations (0-10 µg/ml) of either HuLuc63 or human isotype control $IgG_1$ MSL109 mAbs were added at effector: target (E:T) ratios of 20:1, in a final volume of 200 µl per well. In some experiments, PBMC effector cells were pretreated with lenalidomide for 3 days at 0.2 µM before HuLuc63-mediated ADCC assays were performed. After 4 h incubation, 100 µl culture supernatants were transferred to a Black ViewPlate™-96 plate and arbitrary fluorescent units (AFU) were read on a fluorometer (Wallac VICTOR2). This assay is valid only if (AFU mean maximum release−medium control release)/(AFU mean spontaneous release−medium control release)>7. Calculation of % specific lysis from triplicate experiments was done using the following equation:

$$\% \text{ Specific Lysis} = 100 \times \frac{(AFU \text{ mean experimental release} - AFU \text{ mean spontaneous release}^1)}{(AFU \text{ mean maximal release}^2 - AFU \text{ mean spontaneous release})}$$

[1] Calcein-AM release by target cells in the absence of Ab or NK cells.

[2] Calcein-AM release by target cells upon lysis by detergent.

HuLuc63-mediated lysis of patient MM cells by effector cells from the same patient was measured using an ADCC assay. HuLuc63, but not iso $IgG_1$, induced significant autologous myeloma cell lysis in patients in patient samples (FIGS.

Figure 2A:
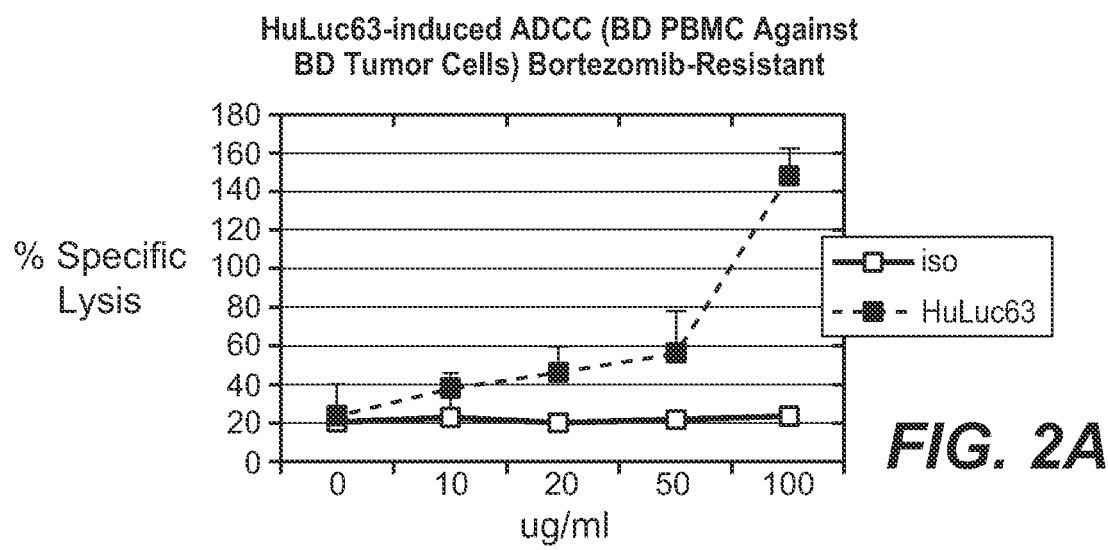
FIGS. 2A-2B depict HuLuc63 induced ADCC against Hsp90 and bortezomib resistant patient tumor cells.
Figure 2B:
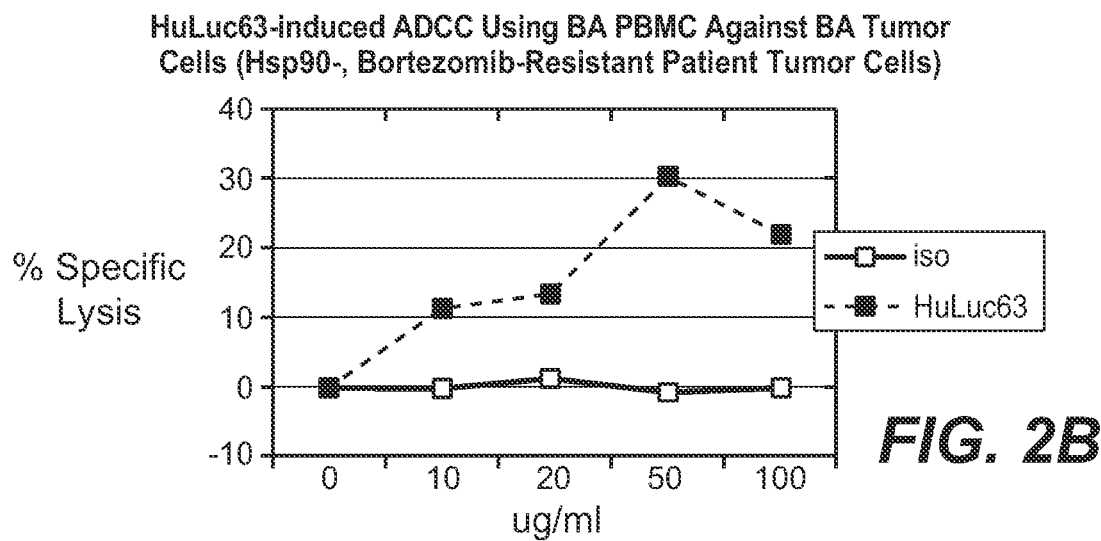

1A-1C). HuLuc63-mediated autologous tumor cell lysis was also demonstrated in patients with MM resistant or refractory to novel anti-MM therapies including bortezomib and/or 17-AAG (targeting heat shock protein 90) (FIGS. 2A and 2B). These data suggest that HuLuc63 can target myeloma cells from patients that are newly diagnosed, or resistant to standard of care drugs and/or novel agents.

Figure 3A:
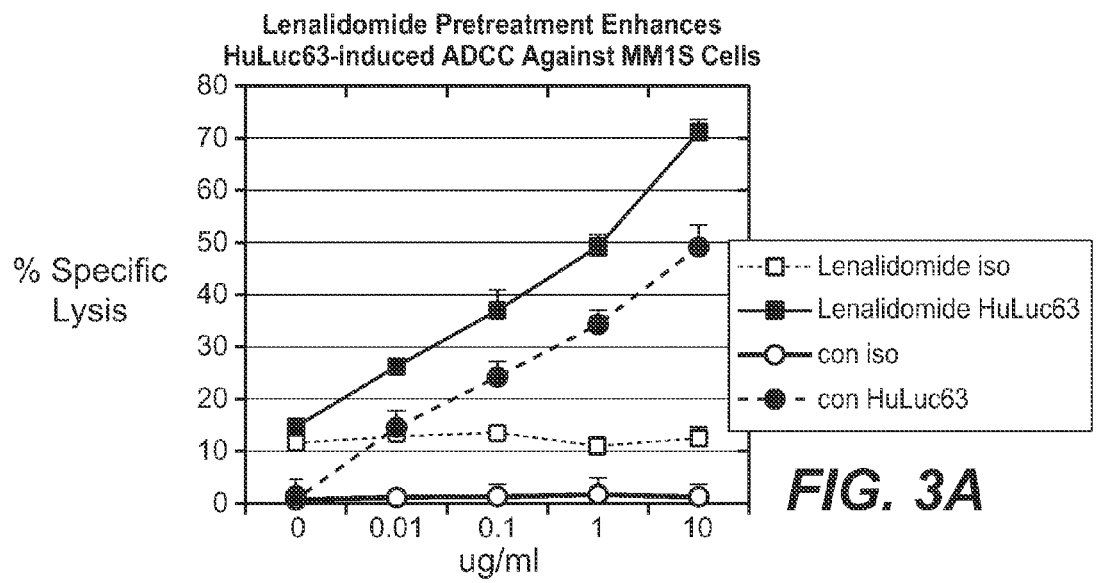
FIGS. 3A-3B depict enhancement of HuLuc63 induced ADCC against MM cells when effector cells were pretreated with lenalidomide.
Figure 3B:
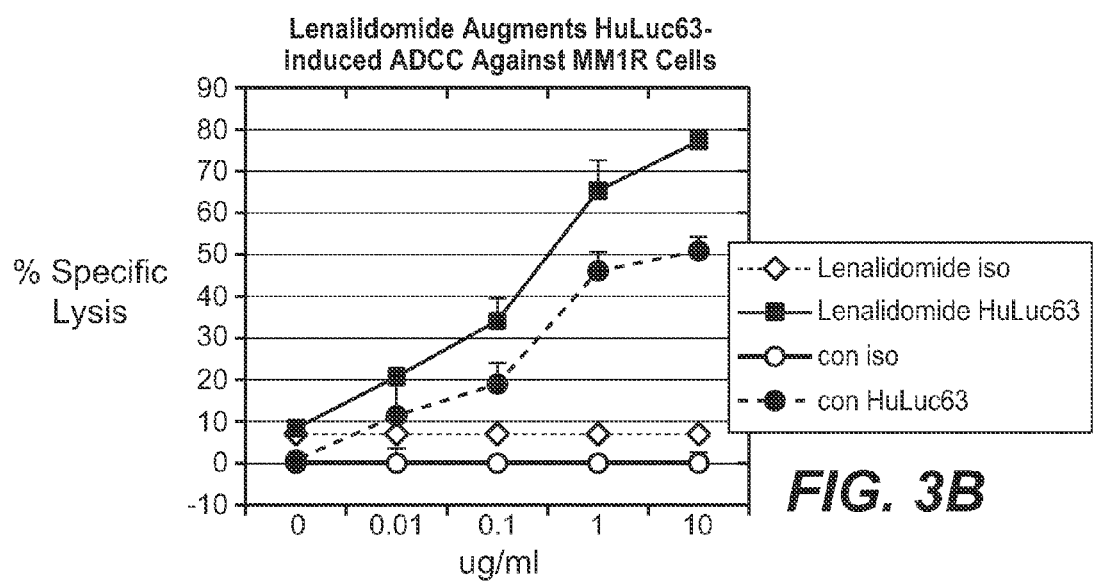
Figure 3C:
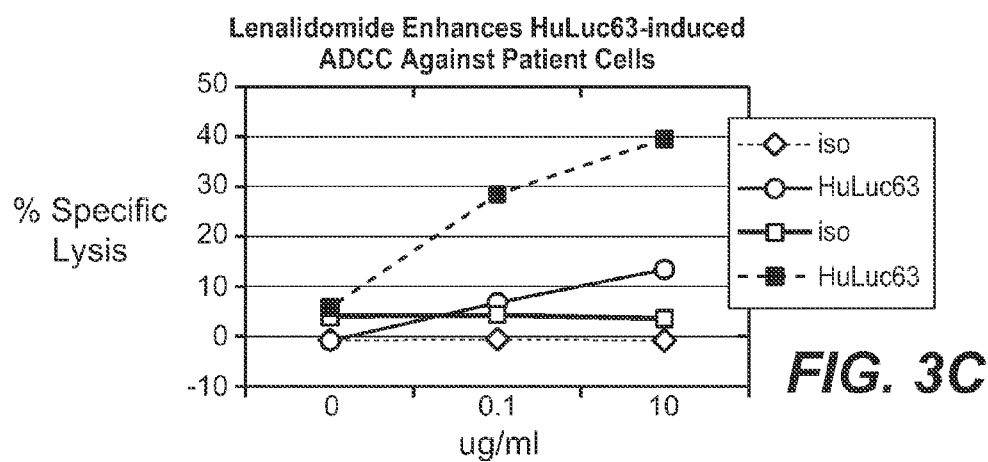
Figure 4A:
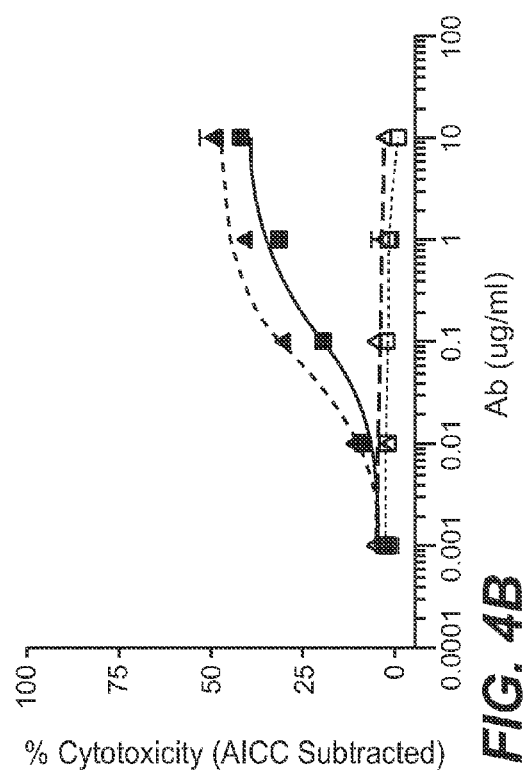
FIGS. 4A-4D depict the effect of bortezomib pre-treatment on HuLuc63-mediated ADCC in vitro. Examples are shown for 4 different donors; and, FIGS. 5A-5B depict the effect of HuLuc63 and bortezomib in OPM2 tumor-bearing mice.
Figure 4B:
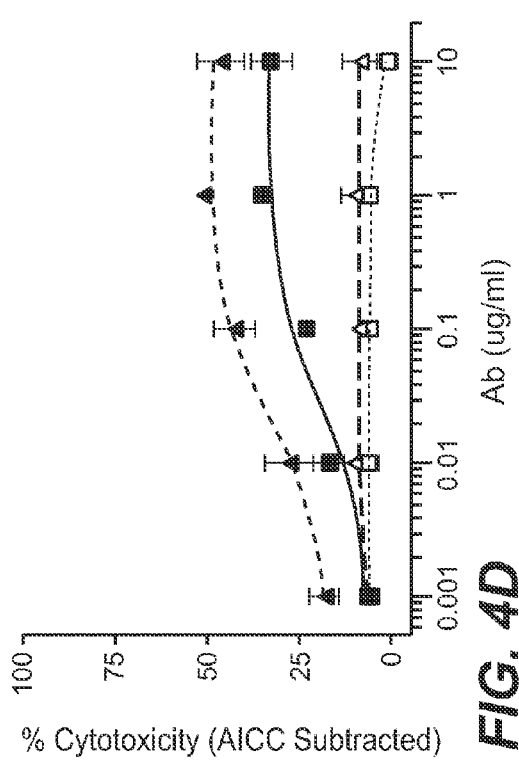
Figure 4C:
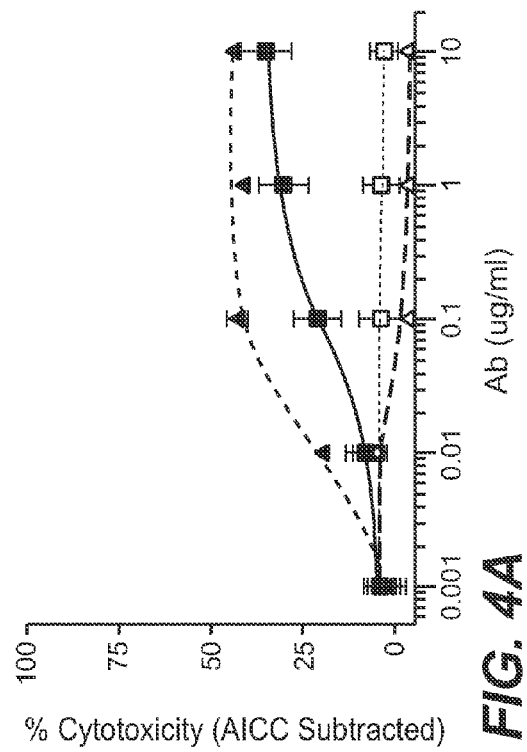
Figure 4D:
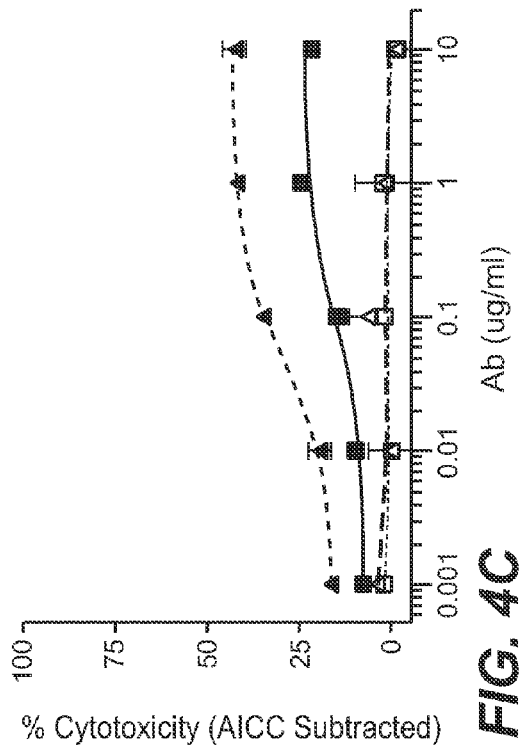

HuLuc63-mediated lysis of patient myeloma cells by PBMC effector cells from the same patient was measured using an ADCC assay. CD138-purified tumor cells from a patient with MM were incubated with autologous effector cells in the presence of serial dilutions of HuLuc63 (solid symbols) or isotype control IgG$_1$ (open symbols). PBMC effector cells were pre-incubated for 3 days in the presence or absence of with lenalidomide (0.2 mM) (square symbols) or vehicle control (round symbols), followed by HuLuc63-mediated ADCC. HuLuc63-mediated ADCC, but not iso IgG$_1$, induced significant autologous myeloma cell lysis in a patient sample. Pre-incubation of the PBMC effector cells with lenalidomide significantly increased the ADCC activity (FIG. 3C). Similarly, pretreatment of effector cells with lenalidomide enhanced HuLuc63-induced lysis of myeloma cell lines (FIGS. 3A and 3B). These results provide the framework for a treatment strategy combining lenalidomide with HuLuc63 in MM.

Example 2

HuLuc63 in Combination with Bortezomib

Bortezomib is a potent, specific, and reversible proteasome inhibitor. Proteasomes are present in all cells and function to help regulate cell growth. Inhibition of the proteasome results in apoptosis of cancer cells. Bortezomib has been shown to be particularly effective at killing myeloma cells and is currently approved for $2^{nd}$ and $3^{rd}$ line therapy in multiple myeloma. Recent data has shown that bortezomib treatment of myeloma cells results in down-modulation of cell-surface expression of MHC class I, an inhibitor of NK function (Shi et al., Blood (ASH Annual Meeting Abstracts), November 2006; 108:3498). The hypothesis is that bortezomib treatment of myeloma cells would make them more susceptible to NK-mediated killing and, thus, enhance HuLuc63-mediated ADCC. The purpose of this study was to examine whether using HuLuc63 in combination with bortezomib provided therapeutic benefit.

The effect of HuLuc63 and bortezomib treatment on expression of CS1 in MM cell lines and mouse xenograft tumors was examined by flow cytometry and immunohistochemistry respectively.

In vitro ADCC Assay: Methods and Results

OPM2 myeloma cells were harvested at mid-log phase, suspended at a density of $1.0 \times 10^6$ cells/mL in complete media (RPMI with 10% FBS) and treated overnight with or without Velcade (10 nM). Cells were collected, washed, re-suspended at a density of 20×106 viable cells/mL, and labeled for one hour with 50 mCi Na$_2$[$^{51}$Cr]O$_4$ per $10^6$ cells. $^{51}$Cr-Labeled cells were washed then added to a 96-well V-bottomed polystyrene plate at a cell density of 15,000 cells per 75 µL RPMI supplemented with 10% heat-inactivated FBS. HuLuc63 and a human IgG$_1$ isotype control antibody MSL-109 were added to target cells for a final antibody concentration ranging from 0.001 to 10 µg/mL. NK cells were enriched from the whole blood of healthy donors using the RosetteSep human NK cell enrichment cocktail (Stem Cell Technologies). The enriched NK cells were added to Velcade treated or untreated OPM2 cells at a ratio of 10:1. After a 4-hour incubation at 37° C., cells were centrifuged and the supernatants measured for released $^{51}$Cr. Maximum release was determined from target cells lysed with 100 mg/ml Digitonin. Antibody independent cellular cytotoxicity (AICC) was determined using target cells, plus media, plus NK cells, while spontaneous lysis was determined using $^{51}$Cr-labelled cells plus media without NK effectors.

% Cytotoxicity was calculated as ((sample−AICC)/(Maximum−AICC)*100.

CS1 protein expression was examined on the OPM2 multiple myeloma cell line with no significant change in CS1 expression observed pre- or post-treatment with HuLuc63, bortezomib or with both agents. The combination of HuLuc63 with bortezomib was then tested for anti-myeloma activity in vitro using ADCC assays. The results showed that pre-treatment with bortezomib significantly enhanced HuLuc63-mediated ADCC towards OPM2 cells using NK effector cells from healthy donors. OPM2 cells were pre-treated with vehicle control (square symbols) or bortezomib (10 nM; round symbols) for 18 hrs and were then subjected to HuLuc63 mediated ADCC using human NK cells from healthy donors. HuLuc63 (closed symbols) and isotype control antibody (open symbols) were used at doses ranging from 0.001-10 µg/ml. The results show that bortezomib pre-treatment significantly decreased the EC$_{50}$ for HuLuc63-mediated ADCC in vitro (FIGS. 4A-4D, Table 3).

TABLE 3

| | No Treatment | Bortezomib (10 nM) | P value (t test) |
|---|---|---|---|
| 1 | 0.0758 | 0.0106 | 0.04 |
| 2 | 0.149 | 0.057 | 0.05 |
| 3 | 0.103 | 0.0459 | 0.004 |
| 4 | 0.0302 | 0.0207 | 0.0004 |

In vivo Xenograft Mouse Model: Methods and Results

Six- to eight-week old female IcrTac:ICR-Prkdc$^{scid}$ mice obtained from Taconic Farms (Germantown, N.Y.) were inoculated with $1 \times 10^7$ OPM2 (American Type Culture Collection) cells into the lower right flank. Caliper measurements were performed twice weekly to calculate tumor volume using the following formula: L×W×H/2, where L (length) is the longest side of the tumor in the plane of the animal's back, W (width) is the longest measurement perpendicular to the length and in the same plane and H (height) is taken at the highest point perpendicular to the back of the animal. When tumors reached an average size of about 100 mm$^3$, animals were randomized into 3 groups of 8-10 mice each and were treated with 1 mg/kg of antibody administered intraperitoneally twice a week for a total of 6 doses. Bortezomib was administered intraperitoneally at a dose of 0.75 mg/kg twice a week for a total of 6 doses. Tumor growth was monitored for a period of 1-2 months. Animal work was carried out under NIH guidelines ("Guide for the Care and Use of Laboratory Animals") using protocols approved by IACUC at PDL BioPharma.

Figure 5A:
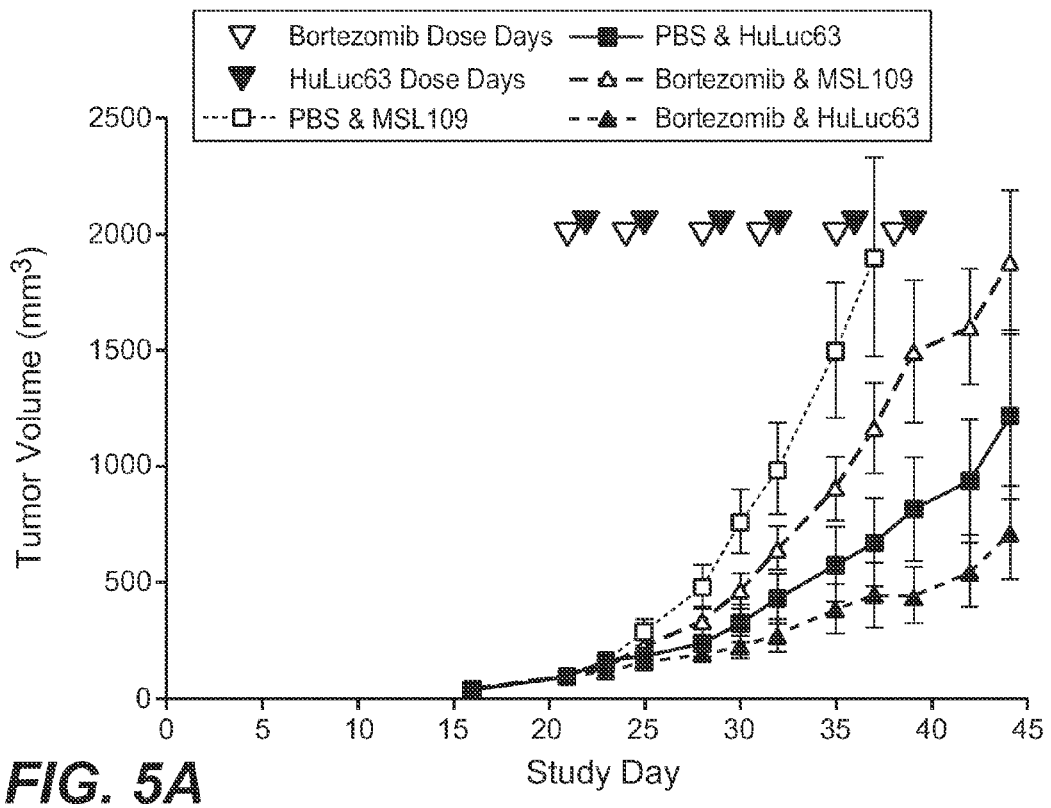

To examine the effect of HuLuc63 combination therapy with bortezomib in vivo, OPM2 tumor-bearing mice were treated with sub-optimal doses of HuLuc63 (1 mg/kg), or isotype control antibody twice weekly for three weeks. Bortezomib was given twice a week at 0.75 mg/kg to mice receiving either isotype control antibody or HuLuc63. The results showed significant anti-tumor activity of HuLuc63 alone and in combination with bortezomib (FIG. 5A). Mice in the combination treatment group exhibited on average 40-50% smaller tumors than in the HuLuc63 monotherapy group, and 60-70% smaller tumors than in the bortezomib group.

In a second experiment, HuLuc63 was combined with bortezomib in vivo, using a different dose and dosing schedule for bortezomib, while keeping the original HuLuc63 dose and dosing schedule. OPM2 cells were inoculated into the flanks of SCID mice. When tumors reached an average size of about 100 mm3, animals were randomized into 4 groups of 15 mice each and were treated with 1 mg/kg of antibody administered intraperitoneally twice a week for a total of 10 doses. Bortezomib was administered intraperitoneally at a dose of 1 mg/kg twice for weeks 1 and 2, no treatment for week 3, and 1 mg/kg twice for weeks 4 and 5 for a total of 8 doses. The intent for this dosing schedule was to more closely mimic the dosing schedule of bortezomib in the clinic, where each treatment cycle consists of 2 weeks of dosing, with one week off. Tumor growth was monitored for a period of 1-2 months.

Figure 5B:
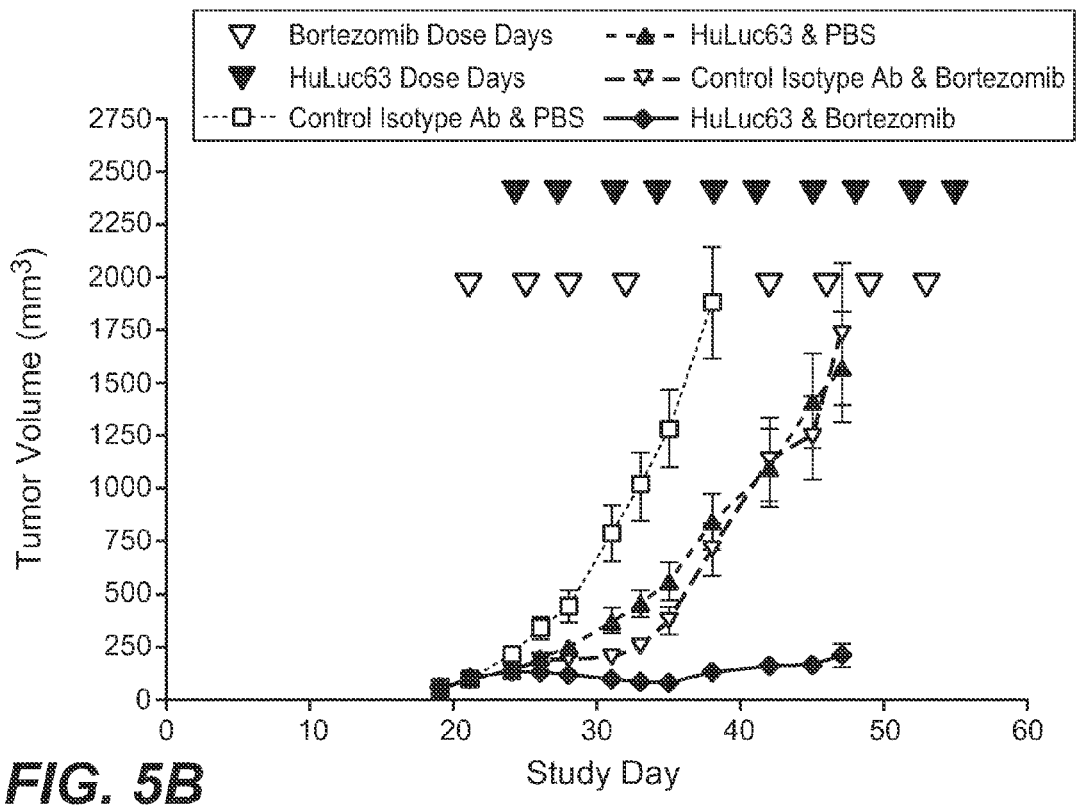

The results showed significant anti-tumor activity of HuLuc63 alone, bortezomib alone and for HuLuc63 in combination with bortezomib (FIG. 5B). Mice in the combination treatment group exhibited significantly smaller tumors than mice treated with either drug alone. The data indicates that bortezomib synergizes with HuLuc63 in anti-myeloma tumor activity.

Example 3

Phase 1b, Open-Label, Dose-Escalation Study of HuLuc63 and Bortezomib in Multiple Myeloma Patients Following First or Second Relapse The proposed Phase 1b, multi-center, open-label, multi-dose, dose escalation study will evaluate the combination of HuLuc63 and bortezomib in patients with multiple myeloma after 1st or 2nd relapse. HuLuc63 will be given by intravenous injection (IV) at up to five dose levels ranging from 2.5 mg/kg to 20 mg/kg in combination with a fixed dose of bortezomib IV at 1.0 mg/m2. Patients will receive HuLuc63 every 10 days and bortezomib will be given in 21-day cycles (twice weekly for two weeks (days 1, 4, 8, 11) followed by a 10-day rest period (days 12-21)).

After 9 weeks of therapy (6 doses of HuLuc63, 3 cycles of bortezomib), EBMT criteria will be assessed. If a patient has progressive disease, HuLuc63 will be discontinued and bortezomib may be withdrawn or continued at the discretion of the site investigator. If the patient has responded or has stable disease at Week 9, dosing with HuLuc63 and bortezomib will continue so that a total of 24 weeks of treatment (16 doses HuLuc63, 8 cycles bortezomib) are completed or disease progression occurs. Dosing with HuLuc63 and bortezomib will continue until the data from the Week 9 visit are available.

Patients will receive HuLuc63 IV once every 10 days, with each dose infused over 1 hour. Bortezomib will be given as IVP for 8 three-week cycles with each cycle consisting of bortezomib on days 1, 4, 8 and 11 followed by a ten-day rest period (days 11-21). Dosing cohorts are as follows: 2.5 mg/kg HuLuc63/1.3 mg/m$^2$ bortezomib; 5 mg/kg HuLuc63/1.3 mg/m$^2$ bortezomib; 10 mg/kg HuLuc63/1.3 mg/m$^2$ bortezomib; 15 mg/kg HuLuc63/1.3 mg/m$^2$ bortezomib; and, 20 mg/kg HuLuc63/1.3 mg/m$^2$ bortezomib.

HuLuc63 will be provided at a concentration of 10 mg/mL in an intravenous formulation in vials. Bortezomib will be provided as a 3.5 mg lyophilized cake or powder in a 10 mL vial, to be reconstituted with 3.5 mL normal (0.9%) saline, sodium chloride injection to 3.5 mL of 1 mg/mL of bortezomib, as per Velcade® package insert.

Approximately 15 to 30 patients in 5 cohorts will be enrolled in the trial. Each cohort will begin with 3 patients. If no dose-limiting toxicity (DLT) is noted within the first 6 weeks of treatment in any patient, enrollment will begin in the next higher cohort. If one patient has a DLT, 3 additional patients will be enrolled in the cohort. If no other patient in the cohort has a DLT, escalation to the next cohort may proceed. If a second patient in a cohort has a DLT, the maximum tolerated dose (MTD) has been reached.

A dose-limiting toxicity (DLT) is defined using the National Cancer Center Institute Common Toxicity Criteria Version 3.0 (NCI CTCAE v3.0) as a grade 4 hematologic toxicity or hyperbilirubinemia, or a grade 3 toxicity in any other system considered related to HuLuc63 or the combination of HuLuc63 and bortezomib. For dose escalation to the next cohort, 3 assessable patients must complete their first 6 weeks (4 doses HuLuc63, 2 cycles bortezomib). If a DLT occurs, an additional three assessable patients will be accrued. Patients will be monitored for safety by assessing adverse events categorized by NCI CTCAE v3.0 and patients will be monitored for clinical activity using EBMT. The maximally tolerated dose (MTD) is defined as the highest dose studied for which the incidence of DLTs is ≤33%. The highest tolerated dose will be HuLuc63 20 mg/kg+bortezomib 1.0 mg/m$^2$ if no dose limiting toxicities are observed.

Example 4

Phase 1b, Multi-Center, Open-Label, Dose-Escalation Study of HuLuc63 and Lenalidomide The proposed Phase 1b, multi-center, open-label, multi-dose, dose escalation study will evaluate the combination of HuLuc63 and lenalidomide in patients with multiple myeloma after 1st or 2nd relapse. HuLuc63 will be given by intravenous injection (IV) at up to five dose levels ranging from 2.5 mg/kg to 20 mg/kg in combination with a fixed dose of lenalidomide PO at 15 mg. Patients will receive HuLuc63 every 7 days and lenalidomide will be given in 28-day cycles (once daily for 21 days followed by a 7-day rest period (days 22-28)).

After 8 weeks of therapy (8 doses of HuLuc63, 2 cycles of lenalidomide), EBMT criteria will be assessed. Dexamethasone will be added to the regimen at an oral dose of 40 mg daily on days 1, 8, 15 and 22 of a 4-week cycle. If at week 12 (12 doses HuLuc63, 3 cycles of lenalidomide, 1 cycle of dexamethasone) there is evidence of progressive disease, HuLuc63 will be stopped and lenalidomide and dexamethasone will be continued up to 16 weeks at the discretion of the investigator. If a patient has stable disease or better, they will continue on HuLuc63 until week 16 (15 total doses) or disease progression. EBMT criteria will be evaluated at week 16.

Patients will receive HuLuc63 IV once every 10 days, with each dose infused over 1 hour. Lenalidomide will be given orally daily for 3 weeks followed by a weeklong rest period. Dosing cohorts are as follows: 2.5 mg/kg HuLuc63/15 mg lenalidomide; 5 mg/kg HuLuc63/15 mg lenalidomide; 10 mg/kg HuLuc63/15 mg lenalidomide; 15 mg/kg HuLuc63/15 mg lenalidomide; and, 20 mg/kg HuLuc63/15 mg lenalidomide. After week 8, dexamethasone will be added to the above regimens at an oral dose of 40 mg daily on days 1, 8, 15 and 22 of a 4 week cycle.

HuLuc63 will be provided at a concentration of 10 mg/mL in an intravenous formulation in vials. Lenalidomide will be supplied as 5 mg and 10 mg capsules for oral administration.

Approximately 15 to 30 patients in 5 cohorts will be enrolled in the trial. Each cohort will begin with 3 patients. If no dose-limiting toxicity (DLT) is noted within the first 4 weeks of treatment in any patient, enrollment will begin in the next higher cohort. If one patient has a DLT, 3 additional patients will be enrolled in the cohort. If no other patient in the cohort has a DLT, escalation to the next cohort may proceed. If a second patient in a cohort has a DLT, the maximum tolerated dose (MTD) has been reached.

A dose-limiting toxicity (DLT) is defined using the National Cancer Center Institute Common Toxicity Criteria Version 3.0 (NCI CTCAE v3.0) as a grade 4 hematologic toxicity or hyperbilirubinemia, or a grade 3 toxicity in any other system considered related to HuLuc63 or the combination of HuLuc63 and lenalidomide. For dose escalation to the next cohort, 3 assessable patients must complete their first 4 weeks (4 doses HuLuc63, 1 cycle lenalidomide). If a DLT occurs, an additional three assessable patients will be accrued. Patients will be monitored for safety by assessing adverse events categorized by NCI CTCAE v3.0 and patients will be monitored for clinical activity using EBMT. The maximally tolerated dose (MTD) is defined as the highest dose studied for which the incidence of DLTs is ≤33%. The highest tolerated dose will be HuLuc63 20 mg/kg+lenalidomide 15 mg if no dose limiting toxicities are observed.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A method of treating multiple myeloma in a subject, comprising administering to a subject in need thereof a first pharmaceutical composition comprising a therapeutically effective amount of HuLuc63, said HuLuc63 being a humanized $IgG_1$ antibody comprising the heavy chain variable region of SEQ ID NO:5 and the light chain variable region of SEQ ID NO:6, a second pharmaceutical composition comprising a therapeutically effective amount of lenalidomide, and a therapeutically effective amount of dexamethasone.

2. The method according to claim 1, in which HuLuc63 is administered intravenously at a dosage from approximately 0.5 mg/kg to approximately 20 mg/kg.

3. The method according to claim 1, in which lenalidomide is administered orally at a dosage from approximately 1 mg/day to 50 mg/day.

4. The method according to claim 1, in which each of said first pharmaceutical composition and said second pharmaceutical composition further comprises a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 8,632,772 B2 | Page 1 of 1 |
| APPLICATION NO. | : 11/835257 | |
| DATED | : January 21, 2014 | |
| INVENTOR(S) | : Anderson et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 857 days.

Signed and Sealed this
First Day of September, 2015

Michelle K. Lee
*Director of the United States Patent and Trademark Office*